United States Patent [19]
Walker et al.

[11] Patent Number: 4,846,812
[45] Date of Patent: Jul. 11, 1989

[54] SOFTENING CATHETER

[75] Inventors: Jack M. Walker, Portola Valley; Ronald C. Brown, Santa Cruz; Joseph R. Thomas, Fremont, all of Calif.

[73] Assignee: Menlo Care, Inc., Palo Alto, Calif.

[21] Appl. No.: 171,563

[22] Filed: Mar. 22, 1988

[51] Int. Cl.[4] ............................................. A61M 5/00
[52] U.S. Cl. .................................. 604/264; 604/265; 604/280; 128/768
[58] Field of Search ......................... 604/93, 164–170, 604/264–265, 280; 128/768, 343

[56] References Cited

U.S. PATENT DOCUMENTS

| 3,566,874 | 3/1971 | Shepherd | 604/265 |
| 4,381,008 | 4/1983 | Thomas et al. | 604/265 |
| 4,596,563 | 6/1986 | Pande | 604/280 |
| 4,636,346 | 1/1987 | Gold et al. | 604/280 |
| 4,668,221 | 5/1987 | Luther | 604/265 X |
| 4,728,322 | 3/1988 | Walker et al. | 604/265 X |

Primary Examiner—Stephen C. Pellegrino
Attorney, Agent, or Firm—Fliesler, Dubb, Meyer & Lovejoy

[57] ABSTRACT

A tubular cannula has distal and proximal end portions, a central passageway from the distal end portion of the proximal portion and a transition section connecting the distal and proximal end portions. The proximal end portion has larger inner and outer diamters and has thicker walls than does the distal end portion. The diameter difference and thickness are effectuated in a gradual manner in a transition section. The cannula is constructed of a material that softens on being inserted into a living body and/or contacted with an aqueous medium. The cannula combines kink resistance external of the living body with the advantages of a softening and generally swellable catheter.

15 Claims, 2 Drawing Sheets

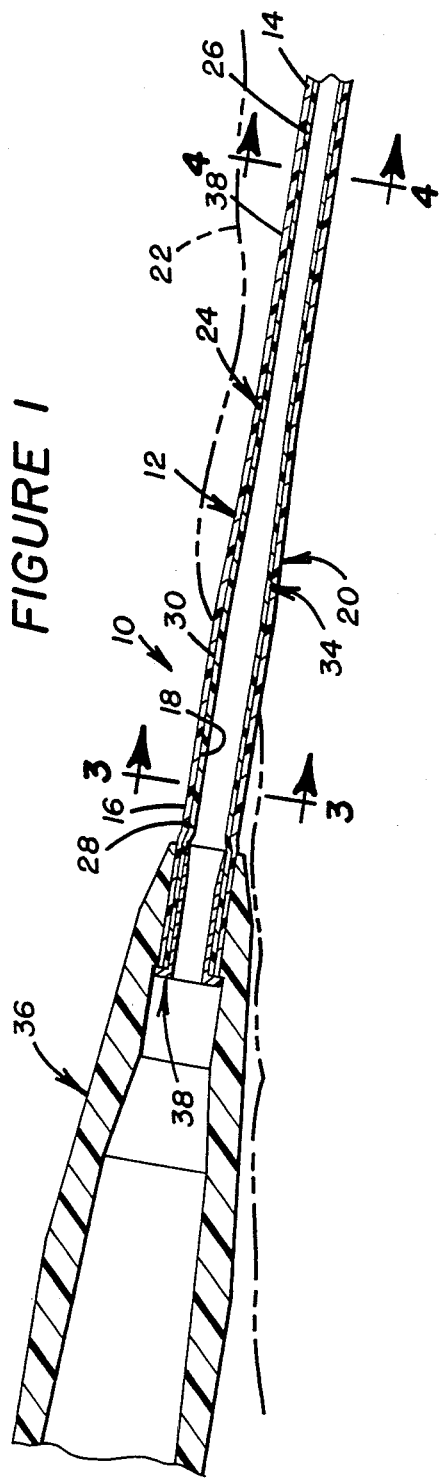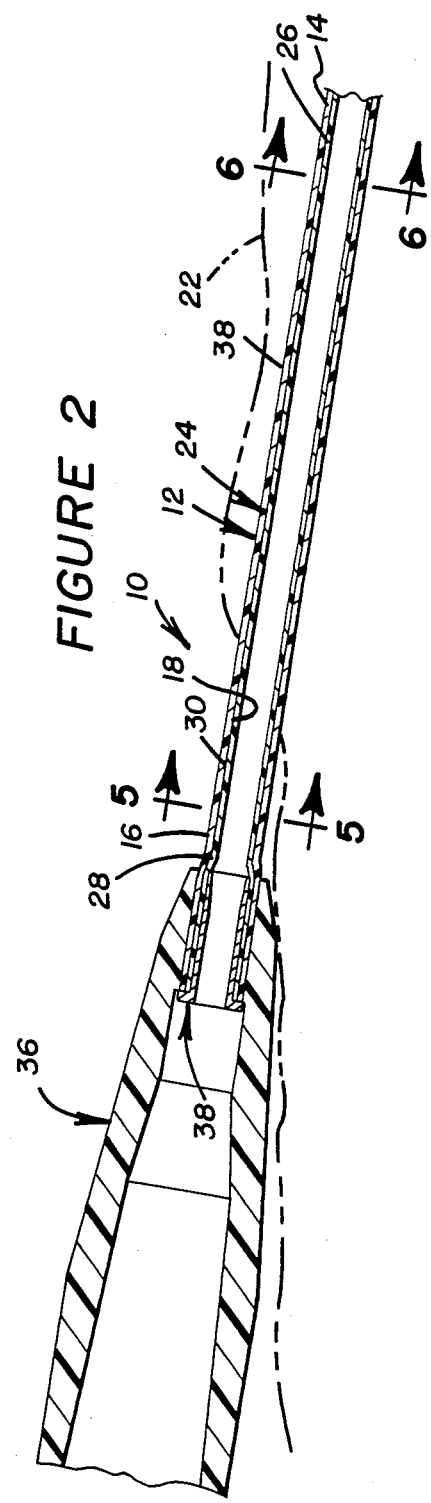

SOFTENING CATHETER

TECHNICAL FIELD

The present invention relates to a cannula structure, the distal end portion of which is inserted in a living subject. More particularly, the invention relates to an over-the-needle type of cannula structure.

BACKGROUND ART

A number of cannula materials are known which will soften significantly on being inserted into a patient due to contact with an aqueous liquid (hydrophilic cannulae) or on being heated to body temperature (shape-memory material). Such cannulae will also usually swell (increase wall thickness and inner and outer diameters) when this occurs. If such cannulae are of a hydrophilic material the swelling is due to uptake of water; if of shape-memory material due to return to a previous thickness and previous diameters on being heated to a glass transition temperature. The use of cannulas which will soften and swell on being contacted with an aqueous liquid, for example on the distal end portion of the cannula being inserted in a blood vessel, has a number of advantages. For example, a relatively small puncture can be made into a blood vessel whereupon, after removal of the needle, the cannula will swell to provide a relatively large internal diameter duct as compared to the size of the needle used. Also, the softening is useful in that trauma is thereby kept relatively low.

Unfortunately, a problem exists with softenable cannulae of the nature just described. This problem is that once the cannulae have softened with a softening ratio of at least 2:1 they become very easily distorted or kinked over the entire distance from where they exit the body to the hub to which their proximal ends are attached.

With non-softening cannulae problems of kinking also exist, but only to a significant extent at the point where the cannula proximal end is attached to the hub. Such problems have been incidentally solved while providing cannulae of desired lubricity (see U.S. Pat. No. 4,381,008, issued Apr. 26, 1983 to J. J. Thomas and N. Sobel) by cannulae which are thicker and of greater diameter just where they attach to the hub. The thickened and larger diameter portion of the cannula does not extend far from the hub, and particularly does not extend into the body, since the only problem encountered relates to kinking at the connection to the hub. With such prior art cannulae the problem of distortion or kinking along the entire length of exposed cannula is either not encountered or is of such little significance as to not be considered a problem at all. This is because these catheters are made from a relatively stiff material having a softening ratio of less than 2:1 whereby the only area of concern is the portion of the cannula as it exits the hub.

The present invention is directed to overcoming one or more of the problems set forth above.

DISCLOSURE OF INVENTION

In accordance with an embodiment of the present invention a cannula structure is set forth for insertion into a living body. The cannula structure comprises a tubular cannula having distal and proximal end portions and a central passageway therethrough from the distal end portion to the proximal end portion. The proximal end portion has larger inner and outer diameters than does the distal end portion and the cannula has a greater thickness along the proximal end portion than along the distal end portion, the proximal end portion extending into the living body. The cannula also includes a transition section connecting the distal and proximal end portions whereat the diameter differences are effectuated in a gradual manner. The cannula is constructed of a material that has a softening ratio of greater than 2:1 on being contacted with an aqueous liquid and/or on being inserted into a living body.

An improved cannula structure as set forth above has the advantage of significantly resisting kinking of the entire length of the cannula structure which is between the point of entry into a patient and the distal end of the hub. In this manner the advantages of a softenable catheter material, namely reduced trauma, and in the case where the material also swells a larger duct size for a given size of needle, are realized without the disadvantage of a significant problem of kinking between the hub and the point of entry into the body.

In accordance with certain embodiments of the present invention the cannula structure can also prevent swelling of the tubular cannula when an aqueous liquid is in the duct but still permits such swelling when an aqueous medium, for example, body tissue, contacts the outer surface of the cannula.

In accordance with still other embodiments of the present invention migration of medicaments from the duct outwardly radially through the cannula to the body can be prevented or controlled in rate.

BRIEF DESCRPTION OF DRAWINGS

The invention will be better understood by reference to the figures of the drawings wherein like numbers denote like parts throughout and wherein:

FIG. 1 illustrates, in side section, a cannula structure in accordance with an embodiment of the present invention immediately following insertion in a living subject (shown in phantom);

FIG. 2 illustrates, the embodiment of FIG. 1 after that portion of the cannula structure within the living subject has softened and swollen;

BEST MODE FOR CARRYING OUT INVENTION

Figure 3:
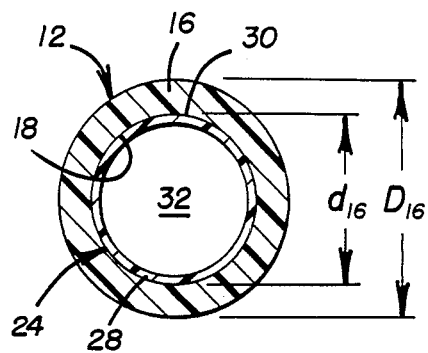
FIG. 3 shows a view taken along the line 3—3 of FIG. 1.

The present invention is directed to an improvement in cannulae which are constructed of a material that softens on being contacted with an aqueous medium by which is meant a water containing medium which may be liquid or solid, e.g., body tissue, which contains water, or upon attaining body temperature. Generally, such materials will also swell on being contacted with the aqueous medium or upon approaching or attaining body temperature. The materials generally soften to a 2.5% Secant Modulus of less than 7,000 N/cm² on being contacted with the aqueous medium or upon attaining body temperature which reduces the trauma to the surrounding tissue of the subject. The term softening ratio is used herein to refer to the ratio of the 2.5% Secant Modulus values of the composition selected in the form of a tubular cannula initially to the 2.5% Secant Modulus of the composition when softened. The material must soften with a softening ration of at least about 2:1, preferably of at least 10:1 and more preferably of at least 20:1 to provide the full advantages of softening cannulae as discussed above.

Examples of softening hydrophilic polymers useful in the practice of the invention are those described in commonly assigned Co-pending application Ser. No. 780,543, filed Sept. 26, 1985, incorporated herein by reference. The preferred composition for the cannula comprises:

(a) a first phase which comprises a substantially non-hydrophilic polymeric component; and (b) a second phase which comprises a hydrophilic polymeric component;

said material (i) being capable of absorbing water to an extent that its softens with a softening ratio of at least about 2:1 and/or swells with a swelling ratio of at least about 1.3:1; and (ii) when substantially completely hydrated, has an energy to break of at least about 700 N-cm/cm$^3$ and a 2.5% Secant Modulus of less than about 7,000 N/cm$^2$.

Also useful are those hydrophilic softening polymers described in U.S. Pat. Nos. 4,359,558; 4,424,305; 4,454,309 and 4,439,583 of Tyndale Plains-Hunter Ltd. incorporated herein by reference. The preferred hydrophilic cannula composition essentially comprises a polyurethane diacrylate composition having from about 90 to about 65 weight percent of a hydrophilic polyurethane resin and from about 10 to about 35 weight percent of a diacrylate.

An alternative material which may be utilized as a cannula material is a thermoplastic composition with softenable and/or shaped-memory properties. Such polymeric compositions are described, for example, in the following articles: Softenable, Shape-Memory Thermoplastics for Biomedical Use, Robert S. Ward, M.D. 7 D, August 1985; and Thrombroresistant, Radioopaque, Softenable Thermoplastics Catheter Compound With Shape-Memory Properties, R. S. Ward, K. A. White, J. S. Riffle, Second World Congress On Biomaterials, 10th Annual Meeting Of The Society For Biomaterials, Washington, D.C., Apr. 27–May 1, 1984. The aforementioned thermoplastic compositions comprise a base polymer that is a block or segmented copolymer thermoplastic with at least one block type with an abrupt effective glass transition temperature ($T_g$) at or greater than room temperature, but less than approximately body temperature. The remainder of the base polymer contains hard blocks whose dominant thermal transition is substantially greater than body temperature. The cannulae can also be made to expand and soften with a softening ratio of at least 2:1 as follows. The cannulae are originally made with their eventually desired expanded internal diameter and then are heated above the glass transition temperature ($T_g$), drawn out to form longer and thinner cannulae and held in this state until cooled below the glass transition temperature. Once the longer and thinner cannulae have warmed to a temperature that is greater than room temperature but less than approximately body temperature, i.e., once the cannulae have reached the glass transition temperature, the shape-memory properties operate and the cannulae increase in internal and external diameter while shrinking in length.

It is also preferred when selecting such softening materials of the cannulae that such materials also swell wherein at least a portion of the cannula inner cross-section of the duct and/or outer circumference of the cannula increases to form an enlarged inner cross-section of the duct and/or enlarged outer circumference of the cannula when inserted in a living subject and maintained therein and/or when the duct is contacted by a liquid for a period of time sufficient for the enlarged duct cross-section and/or outer circumference to form. Preferably, the duct cross-section increases from about 25% to about 400%.

The composition of the preferred cannula may be cross-linked if desired. Cross-linking gives the composition strength wherein the melting or softening points of the uncross-linked polymeric components permit sterilization of the catheter assembly using a cannula of such composition at above such temperature. Cross-linking of the material selected for the cannula may also be used to adjust the 2.5% Secant Modulus of the composition to a desired value. Cross-linking may also increase the tensile energy to break of the material which has been softened. Cross-linking can also be used to minimize extractable components of the composition. Cross-linking can be effected by use of an appropriate cross-linking agent or by radiation, preferably in the presence of a cross-linking promoter, such as triallyl isocyanurate or the like. Or, the material can be cross-linked by high energy gamma or beta radiation.

The material of the cannula may contain additional ingredients such as stabilizers, antioxidants, radioopacifiers, medicaments, fillers or the like. For certain applications it may be advantageous to incorporate a water soluble or water dispersible medicament which can leach from the material when it contacts the aqueous media of the living subject. Such medicaments include anti-thrombogenic agents, antibiotics, antiviral agents, anticoagulants, antiinflamatory agents, and the like.

A cannula selected such that it swells and/or softens should not do so appreciably during the time it is being inserted in a living subject or the like. It is preferable that such cannulae's swelling or softening time should be at least about 15 seconds and preferably at least about 60 seconds. The swelling of the cannula has several advantages. Swelling of the cannula permits insertion of a smaller device for equivalent fluid flow and/or can result in pressure around a wound site reducing bleeding and bacterial invasion into the wound and prevent catheter slip out, a common cause for changing catheters prematurely. Increased cross-section of the cannula duct also permits increased flow through the cannula when compared with similar non-swelling cannula of identical initial dimensions. This allows access to smaller areas such as the veins in the limbs and easier insertion into the selected site. A soft cannula tends to cause less irritation to the intima (lining of the vein) and to the insertion site and is less likely to contribute to mechanical phlebitis. The softness of the cannula also permits it to float in a vein rather than lie on the point where inserted and consequently any infusion is delivered evenly helping to advert chemical phlebitis.

Once the cannula is selected, a needle is selected having distal and proximal ends and having a sharpened insertion tip at the distal end. The needle may be selected to be either hollow or solid, that is, the term needle is used broadly to cover hollow or solid longitudinal piercing members. The needle is positioned within the distal end portion of the longitudinal duct of the cannula with the insertion tip extending beyond the distal end of the cannula. An extraction wire, rod, etc., may optionally be attached to the proximal end of the needle and extend outward to the proximal end of the cannula. Extraction of the needle may be accomplished by pulling the extraction wire.

The catheter assembly further comprises a cannula hub portion. The hub portion has a passageway therethrough from the proximal end portion to the distal end portion of the hub and has appropriate attaching means for attaching the proximal end portion of the cannula to the distal end of the hub with the passageway in flow communication with the duct in the proximal end portion of the cannula. Many such hubs are known in the prior art and are suitable for the invention. Where the cannula material is a swellable material it is desirable to have a hub assembly which will prevent restriction of flow in cannula and will accommodate the expansion. Such a hub is described in commonly assigned U.S. patent application Ser. No. 788,461 filed Oct. 17, 1985, incorporated herein by reference.

Adverting now to the figures of the drawings a cannula structure 10 is illustrated in FIGS. 1 and 2 which comprises a tubular cannula 12 having a distal end portion 14 and a proximal end portion 16. The tubular cannula 12 is made of one of the aforementiond materials which softens on being contacted with an aqueous medium and/or being brought to body temperature. A central passageway 18 proceeds through the tubular cannula 12 from its distal end portion 14 to its proximal end portion 16.

Figure 4:
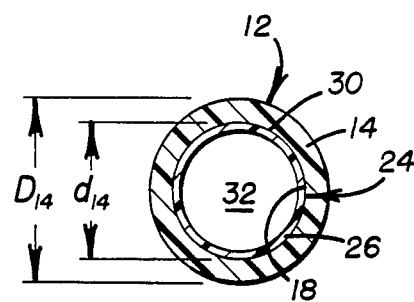
FIG. 4 illustrates a view taken along the line 4—4 of FIG. 1.

In accordance with the present invention, and as will be seen in FIGS. 1, 3 and 4, the proximal end portion 16 of the tubular cannula 12 has larger inner and outer diameters, $d_{16}$ and $D_{16}$, respectively, than does the distal end portion 14, $d_{14}$ and $D_{14}$, respectively. The tubular cannula 12 also has a greater thickness along the proximal end portion 16 than it does along the distal end portion 14 as may be seen by comparing FIGS. 3 and 4. The proximal end portion 16 extends to the point of entry of the cannula 12 into a patient whereby the entire exposed portion of the cannula 12 resists kinking. A tapered transition section 20 (FIG. 1) connects the distal end portion 14 of the tubular cannula 12 to the proximal end portion 16 thereof. In the tapered section 20 the diameter (and generally the thickness) differences are effectuated in a gradual manner.

Figure 5:
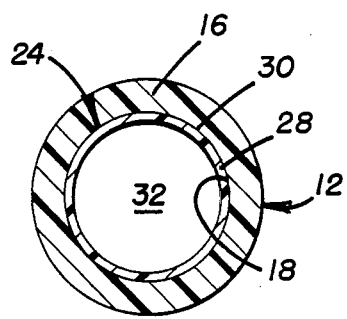
FIG. 5 illustrates a view taken along the line 5—5 of FIG. 2.
Figure 6:
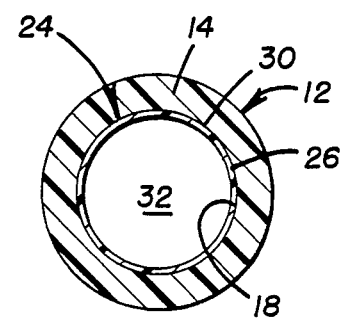
FIG. 6 illustrates a view taken along the line 6—6 of FIG. 2.

FIGS. 2, 5 and 6 show the same cannula 12 as is illustrated in FIG. 1, but only after the distal end portion 14 of the tapered cannula 12 has been in a living subject 22 for a sufficient period of time for it to have softened with a softening ratio of at least 2:1, and, in the embodiment illustrated, swollen. As a result, the thickness of the distal end portion 14 has been increased due to the hydrophilic or shape-memory nature of the material from which the tubular cannula 12 is constructed. Note that the thickness of the tubular cannula 12 at the distal end portion 14 is not necessarily identical, after swelling, to the thickness of the proximal end portion 16 of the tubular cannula 12.

In accordance with an embodiment of the present invention the tubular cannula 12 also includes a tubular inner section (or layer) 24 having a distal end portion 26 and a proximal end portion 28. The tubular inner section 24 has an outer surface 30 which is bonded to the passageway 18 along its length. A central duct 32 is defined by the tubular inner section 24 as illustrated in FIGS. 1–6.

The proximal end portion 28 of the inner section 24 has larger inner and outer diameters than does its distal end portion 26. In general, the inner section 24 has a greater thickness along its proximal end section 28 than along its distal end portion 26. However, this is not a necessity and only occurs because of drawing out of the distal end portion 26 which leads a corresponding thinning of the inner section 24 at the distal end portion 26. A tapered transition section 34 of the inner section 24 serves to connect the proximal end portion 28 with the distal end portion 26 thereof. Along the tapered section 34 the diameter differences (and thickness differences, as appropriate) are effectuated in a gradual manner.

In accordance with an embodiment of the present invention the inner section 24 can be formulated of an inner section material that is substantially water impermeable. This retards or prevents softening of that portion of the cannula 12 exterior of the patient. It is essential that the inner section 24, if present, be of a construction and flexibility such that it yields sufficiently to remain bonded to the passageway 18 and to expand with the cannula material as it softens and swells. The overall resulting increase in cross-section of the duct 32 of the cannula structure 10 should remain in the range from about 25% to about 400%.

Referring to FIGS. 5 and 6 it will be noted that the inner section 24 is considerably thinner in FIG. 6 over that shown in FIG. 5. This happens even if the inner section 24 is originally of similar thickness along its length as shown in FIGS. 3 and 4, since, as the distal end portion 14 of the tubular cannula 12 expands the distal end portion 26 of the inner section 24 must stretch out and cover the enlarged inner diameter without introduction of additional material. The inner section 24 can be made of a material which has a higher Secant modulus than the cannula material on being contacted by an aqueous medium and/or on expanding on reaching body temperature. In such cases additional reinforcement is provided which provides additional resistance to distortion or kinking of the portion of the cannula structure 10 which extends from the living being to a hub 36 to which the distal end portion 16 of the tubular cannula 12 is attached, for example, as illustrated utilizing a small flow through retaining rivet or eyelet 38.

In accordance with an embodiment of the present invention the tubular inner section 24 can be made of a material which is substantially impermeable to medicaments instead of, or in addition to, water. The term medicaments is used to indicate substantially any pharmaceutical which can be introduced through the cannula structure 10, including, for example, anti-thrombogenic agents, antibiotics, antiviral agents, anti-coagulants, anti-inflamatory agents, anti-cancer agents, anesthetics, pain killers, muscle relaxants, tranquilizers, and the like. In this manner any medicaments which are being introduced to the patient can be prevented from diffusing readily outwardly through the cannula structure 10 and contacting the skin whereat irritation may result.

In the figures the structure illustrated includes a tubular cannula 12 having a tubular inner section 24. However, it should be realized that a useful cannula structure 10 results without the presence of the tubular inner section 24. That is, the kinking problem between the hub 36 and the living subject is significantly reduced if all that is done is to provide a greater thickness along the proximal end portion 16 than along the distal end portion 14.

The presence of a water impermeable tubular inner section 24 serves yet another purpose when the cannula 12 is made of a hydrophilic material. In particular, it assures that only that portion of the tubular cannula 12 which is inserted in the living body, and which has its outer surface 38 in contact with an aqueous medium (water containing body tissue), will soften significantly. Thus, in the embodiment illustrated that portion of the cannula structure 10 which is between the hub 36 and the living body does not usually swell since water cannot pass through the water impermeable inner section 24 to enter the hydrophilic material at the proximal end portion 16. Of course some moisture may be picked up from the air over a period of time or due to spillage which makes practice in accordance with the invention desirable but, as a practical matter, the portion of the tubular cannula 12 which is exterior of the living body does not significantly soften for at least a period of time and thus its likelihood of kinking is significantly reduced. A combination of this with the use of a thicker proximal end portion 16 greatly increases the short and long term resistance to kinking.

A number of materials can be utilized as the inner section material. For example, when it is desired to have a water impermeable inner section 24 the inner material may be made of polyurethane, silicone rubber, latex rubber or any other elastomeric or plastic material with sufficient elongation to allow sufficient expansion so that the cannula structure 10 expands 25% to 400% in the cross-section of the duct 32. The same materials are generally medicament impermeable, as well, whereby both water and medicament impermeability are provided.

It is important that the inner section 24, prior to swelling of the cannula 12, not be too resistant to stretching or it will overly restrict the expansion of the passageway 18. The particular thickness acceptable for the inner section 24 varies dependent upon the particular material chosen for the inner section material. For example, very soft and rubbery inner sections 24 can be thicker than stiffer inner sections 24. Generally, however, the inner section 24 will be of a thickness from about 50% to about 0.1%, more preferably from about 20% to about 0.1% and still more preferably from about 15% to about 1% of the total thickness of the cannula structure 10.

A cannula 12 can be formed of the shape shown in FIG. 1 by drawing out the distal end portion 14 of an originally uniform diameter and thickness tube. The result of this is that the distal end portion 14 is somewhat thin (as is the distal end portion 26 of the inner section 24). Also, in the transition section 20 the change in diameter and in thickness occurs in a graduated manner. Of course one starts out with a thick enough cannula 12 in the first place so that the drawn out portion (the distal end portion 14) has sufficient thickness to provide proper structural integrity after being drawn out. If no inner section 24 is present, the tubular cannula 12 can still be made by drawing out the distal end portion 14. All of this can be accomplished by conventional tube drawing techniques. Basically, the tube is heated sufficiently to flow and a longitudinal force is provided to stretch the cannula structure 10 longitudinally. The result is a longer, thinner walled and reduced diameter for the distal end portion 14. The cannula structure 10 can also be heated and formed upon a shaped mandrel.

The tubular cannula 12 may be of any of any convenient thickness depending on the particular cannula material selected. However, it is generally preferred that the wall thickness of the proximal end portion 16 of the tubular cannula 12 be from about 0.5 mm to about 0.1 mm, more preferably from about 0.3 mm to about 0.1 mm.

INDUSTRIAL APPLICABILITY

The present invention is directed to a cannula structure 10 useful for insertion into the blood stream of a living subject and through which medicaments and/or nutrients can be fed and/or through which samples can be extracted.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:

1. A cannula structure for insertion into a living body, comprising:

a tubular cannula having distal and proximal end portions, a central passageway therethrough from the distal end portion to the proximal end portion, the proximal end portion having larger inner and outer diameters than does the distal end portion, the cannula having a greater thickness along the proximal end portion than along the distal end portion, the proximal end portion extending to within the living body, and a transition section connecting the distal and proximal end portions whereat the diameter differences are effectuated in a gradual manner, the cannula being constructed of a material that has a softening ratio of greater than 2:1 on being contacted with an aqueous liquid and/or upon insertion into a living body.

2. A cannula structure as set forth in claim 1, wherein the material swells as it softens.

3. A cannula structure as set forth in claim 1, wherein said softening ratio is at least about 10:1.

4. A cannula structure as set forth in claim 3, wherein the material swells as it softens.

5. A cannula structure as set forth in claim 1, wherein the material has a 2.5% Secant Modulus of less than 7000 N/cm$^2$ on softening.

6. A cannula structure as set forth in claim 1, wherein the material is hydrophilic.

7. A cannula structure as set forth in claim 6, wherein the material swells as it softens.

8. A cannula structure as set forth in claim 7, wherein said tubular cannula further includes:

a tubular inner section having distal and proximal end portions, an outer surface and a central duct, said outer surface being bonded to said passageway along its length, said proximal end portion of said inner section having larger inner and outer diameters than its distal end portion, and a transitional section connecting its proximal and distal end portions whereat the diameter differences are effectuated in a gradual manner, the inner section being formulated of an inner section material that is substantially water impermeable and is of a construction and flexibility such that it yields sufficiently to remain bonded to the passageway and does not prevent the hydrophilic material from expanding as it softens.

9. A cannula structure as set forth in claim 8, wherein the hydrophilic material comprises:
   (a) a first phase which comprises a substantially non-hydrophilic polymeric component; and
   (b) a second phase which comprises a hydrophilic polymeric component; said material (i) being capable of absorbing water to an extent that it softens with a softening ratio of at least about 2:1 and/or swells with a swelling ratio of at least about 1.3:1; and (ii) when substantially completely hydrated, has an energy to break of at least about 700 N-cm/cm$^3$ and a 2.5% Secant Modulus of less than about 7,000 N/cm$^2$.

10. A cannula structure as set forth in claim 8, wherein said inner section material is substantially medicament impermeable.

11. A cannula structure as set forth in claim 8, wherein said inner section, prior to swelling of the cannula, is from about 50% to about 0.1% of the thickness of the cannula.

12. A cannula structure as set forth in claim 6, wherein the hydrophilic material comprises:
   (a) a first phase which comprises a substantially non-hydrophilic polymeric component; and
   (b) a second phase which comprises a hydrophilic polymeric component; said material (i) being capable of absorbing water to an extent that it softens with a softening ratio of at least about 2:1 and/or swells with a swelling ratio of at least about 1.3:1; and (ii) when substantially completely hydrated, has an energy to break of at least about 700 N-cm/cm$^3$ and a 2.5% Secant Modulus of less than about 7,000 N/cm$^2$.

13. A cannula structure as set forth in claim 6, wherein said tubular cannula further includes:
   a tubular inner section having distal and proximal end portions, an outer surface and a central duct, said outer surface being bonded to said passageway along its length, said proximal end portion of said inner section having larger inner and outer diameters than its distal end portion, and a transitional section connecting its proximal and distal end portions whereat the diameter differences are effectuated in a gradual manner, the inner section being formulated of an inner section material that is substantially medicament impermeable and is of a construction and flexibility such that it yields sufficiently to remain bonded to the passageway and to allow the expansion of the cannula as the cannula softens and expands.

14. A cannula structure as set forth in claim 13, wherein the hydrophilic material comprises:
   (a) a first phase which comprises a substantially non-hydrophilic polymeric component; and
   (b) a second phase which comprises a hydrophilic polymeric component; said material (i) being capable of absorbing water to an extent that it softens with a softening ratio of at least about 2:1 and/or swells with a swelling ratio of at least about 1.3:1; and (ii) when substantially completely hydrated, has an energy to break of at least about 700 N-cm/cm$^3$ and a 2.5% Secant Modulus of less than about 7,000 N/cm$^2$.

15. A cannula structure as set forth in claim 1, wherein the material is a thermoplastic composition with shape-memory properties.

* * * * *